United States Patent [19]

Wang et al.

[11] Patent Number: 5,206,350

[45] Date of Patent: Apr. 27, 1993

[54] SYNTHETIC PROCESS FOR THE PREPARATION OF ANTI-TUMOR AGENT-ETOPOSIDE

[75] Inventors: Zhi-guang Wang; Wei-yong Ma; Chun-nian Zhang, all of Shanghai, China

[73] Assignee: Shanghai Institute of Pharmaceutical Industry, Shanghai, China

[21] Appl. No.: 711,900

[22] Filed: Jun. 7, 1991

[30] Foreign Application Priority Data

Jun. 7, 1990 [CH] Switzerland ................... 90102873

[51] Int. Cl.$^5$ .................. C07H 17/04; C07H 1/00; A61K 31/70
[52] U.S. Cl. .................. 536/18.1; 536/18.2; 536/18.5
[58] Field of Search ............. 514/25, 27; 536/17.1, 536/18.1, 18.2, 18.5

[56] References Cited

U.S. PATENT DOCUMENTS

| | | | |
|---|---|---|---|
| 3,408,441 | 10/1968 | von Wartburg et al. | 514/27 |
| 3,524,844 | 8/1970 | Keller-Juslen et al. | 536/18.1 |
| 4,547,567 | 10/1985 | Umezawa et al. | 536/17.2 |
| 5,036,055 | 7/1991 | Ohnuma et al. | 536/18.1 |
| 5,081,234 | 1/1992 | Ohnuma et al. | 536/17.1 |

OTHER PUBLICATIONS

Arnold et al; The Lancet II; 912-915 (Oct. 24, 1981).
Saito et al.; Chemistry Letters 5:799-802 (1987).
Allevi et al.; Tetrahedron Letters 32(47):6927-6930 (Nov. 18, 1991).

*Primary Examiner*—Johnnie R. Brown
*Assistant Examiner*—Nancy S. Carson
*Attorney, Agent, or Firm*—Birch, Stewart, Kolasch & Birch

[57] ABSTRACT

This invention relates to a new synthetic process for the preparation of anti-tumor agent Etoposide (VP16-213). the process, which has shorten reaction route, simple procedure, high yield and low materials cost, therefore facilitates the commercial manufacture of etoposide.

2 Claims, No Drawings

SYNTHETIC PROCESS FOR THE PREPARATION OF ANTI-TUMOR AGENT-ETOPOSIDE

FIELD OF THE INVENTION

The present invention relates to a new synthetic process for the preparation of the anti-tumor agent etoposide.

BACKGROUND OF THE INVENTION

Etoposide (VP16-213), a semi-synthetic anti-tumor drug, is used effectively for the treatment of acute monocytic leukemia (Schilling's leukemia) as well as medullary monocytic leukemia, and has also been proved to be effective to a certain extent for treatment of recticulum cell sarcoma, tissue-cellular lymphoma, lymphosarcoma and Hodgkin's disease. In the therapy for solid carcinoma, etoposide has shown potent activity to small cell carcinoma of lung as well as testical cancer, and is said to be also effective against mastocarcinoma, carcinoma of urinary bladder and thyroid cancer. This drug may be used in combination with a variety of the other antitumor agents, to result in more satisfactory anti-tumor efficacy.

Some synthetic processes have been proposed in the previous literatures such as that reported by kuhn, Max et al in Swiss Pat. 514,578 (1971), which showed the following reaction Scheme (1)

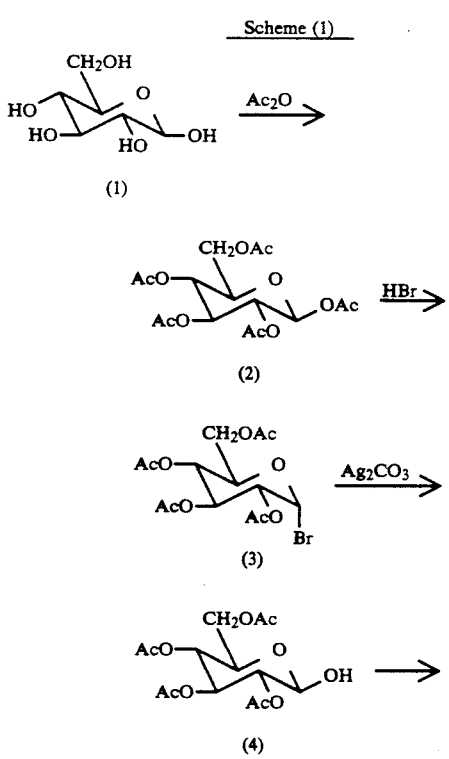

-continued
Scheme (1)

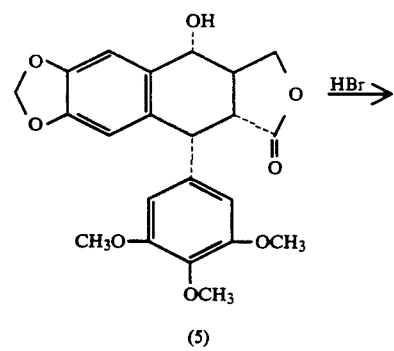

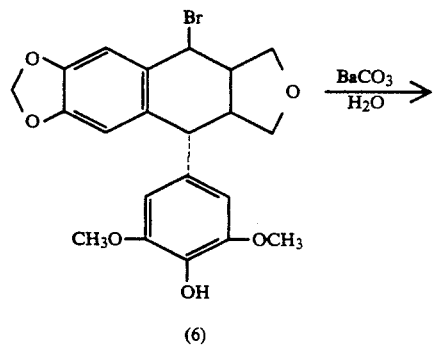

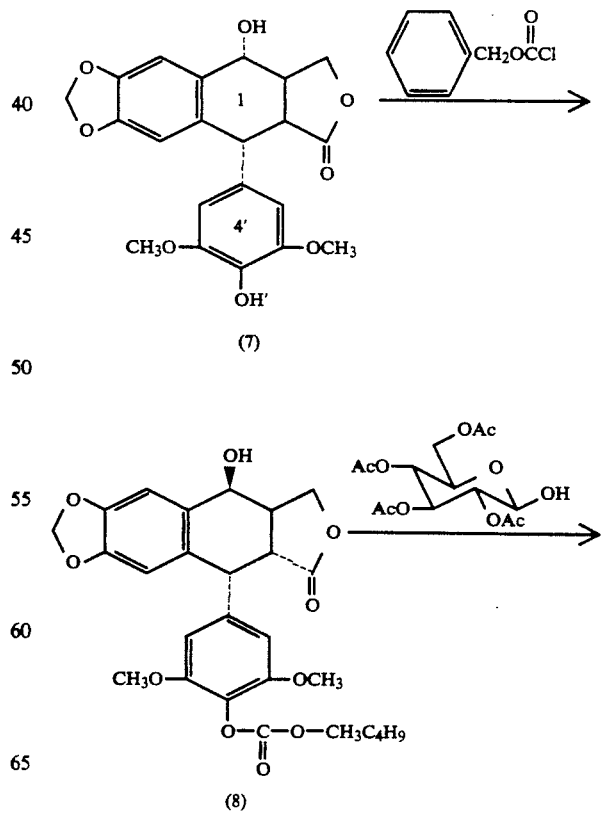

5,206,350
-continued
Scheme (1)
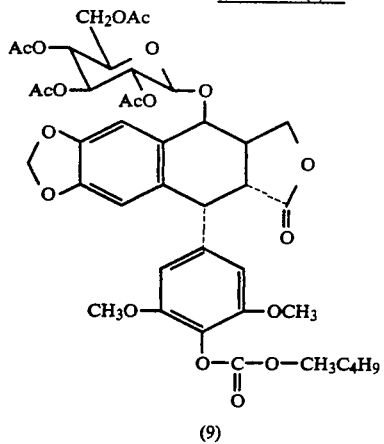
(9)
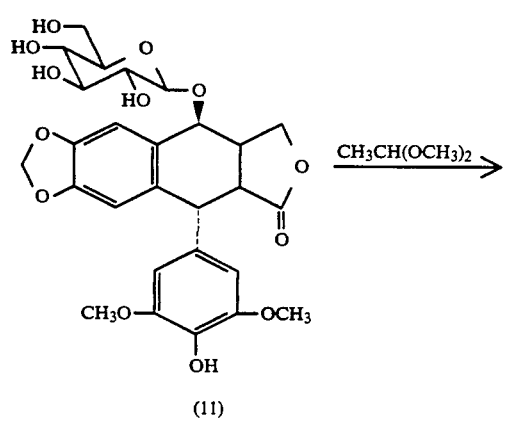
(11)
-continued
Scheme (1)
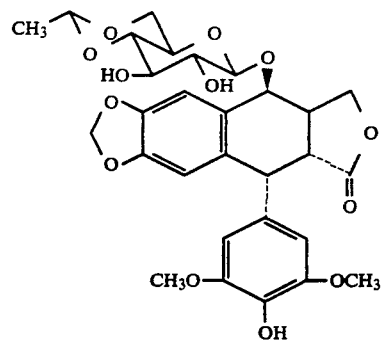
It can be seen the above process includes long reaction pathway, a complex procedure and provides a low yield (only 18% based on 4-demethylepipodophyllotoxin).
Kurabayashi and Kalsuhiko et al reported in JP84-98098 another synthetic process, which included the following reactions (Scheme 2).
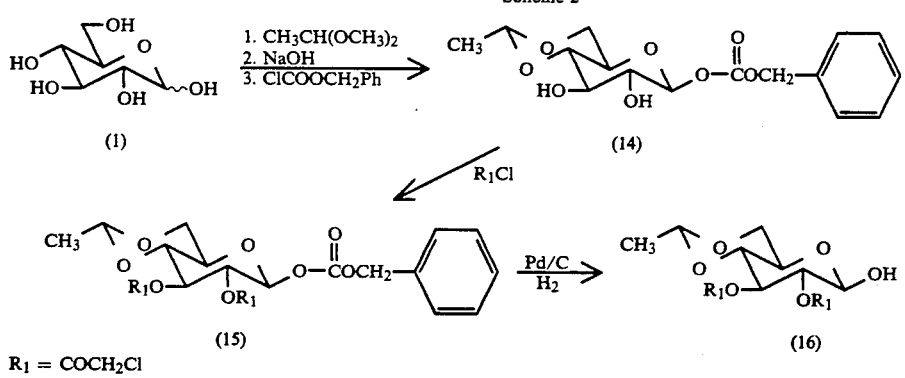
$R_1 = COCH_2Cl$
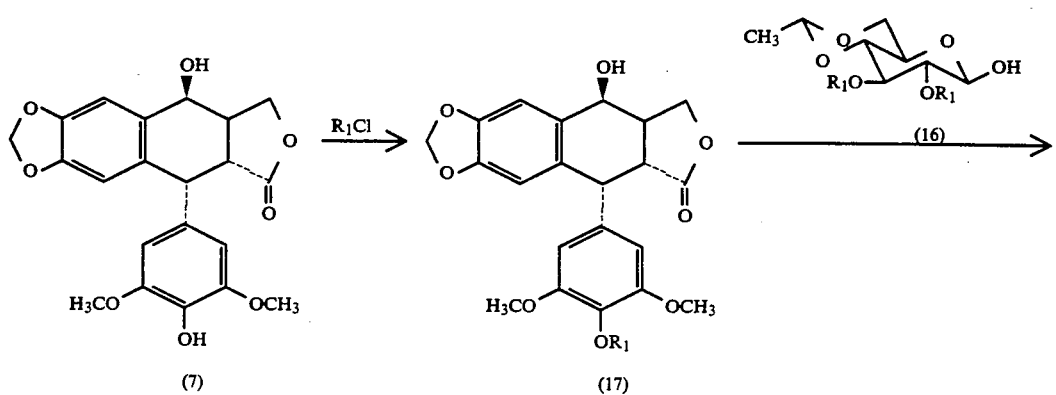

-continued
Scheme 2

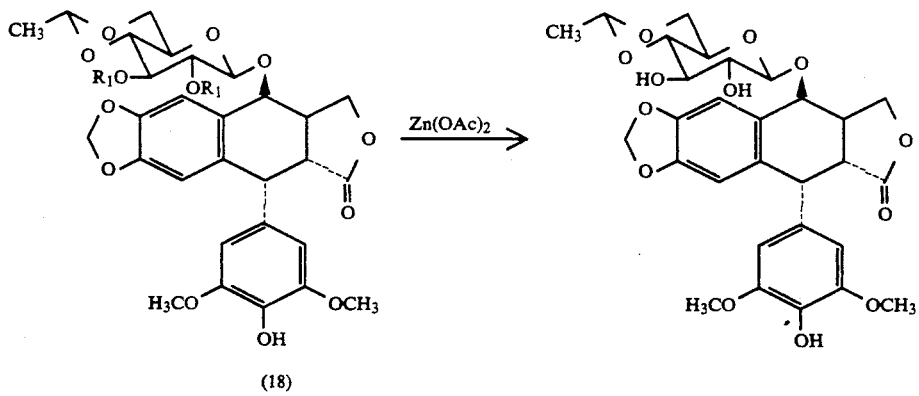

(18)

As compared with the above described method of Max et al, appreciable improvements in this synthetic process are obtained, such as the utilization of same protective group for both the phenolic hydroxy and the hydroxy groups in the sugar moiety, shorter reaction pathway, increased yield. However, Reaction Scheme (2) presents inconveniences. For example, strict conditions are required for controlling monoacylation of the phenolic hydroxy from compound 7 to 17. As such, it follows that the process should be improved.

SUMMARY OF THE INVENTION

In the process of the present invention, 4'-demethylepipodophyllotoxin-4-(2,3-di-O-chloroacetyl-4,6-O-ethylidene)-β-D-pyranoglucoside 19, is produced in a ;yield of 60% by direct condensation of 4'-demethylepipodophyllotoxin 7 and the compound 16 at a temperature below 0° to 30° C. in the presence of boron trifluoride-etherate as catalyst. Then, after removing the chloroacetyl protective group from the compound 18 with zinc acetate in methanol at 80° to 85° C. for 2 hours, the product etoposide is obtained in yield of 90%. The overall yield is 54% on the basis of 4'-demethylepipodophyllotoxin.

The synthetic process of the present invention is as follows:

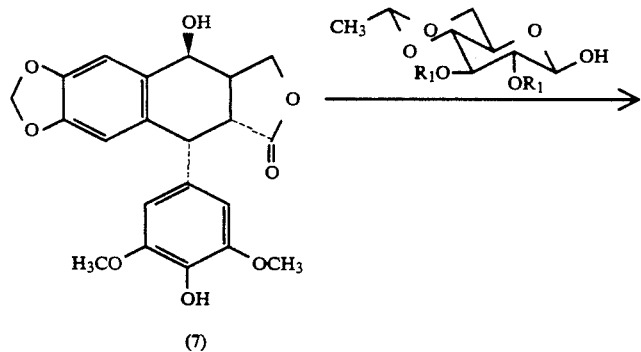

(7)

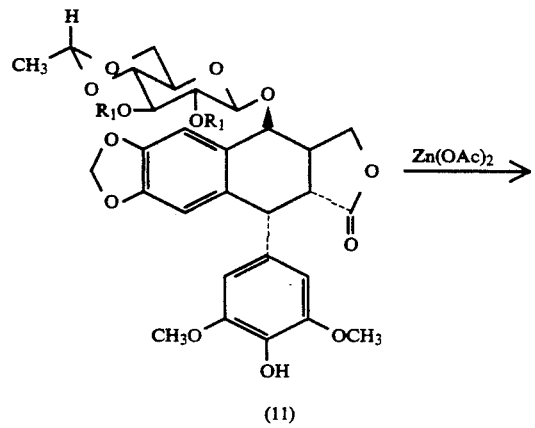

(11)

-continued

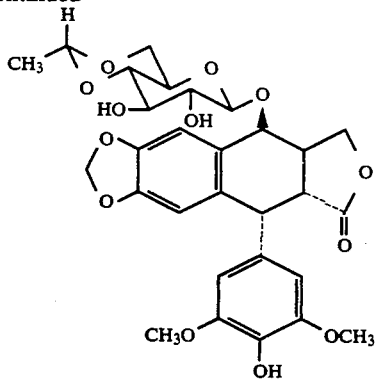

R₁ = COCH₂Cl

DETAILED DESCRIPTION OF INVENTION

The synthetic process of the present invention has the following advantages that are:
1. The reaction route is shorter compared with the above mentioned synthetic processes. The protection of the 4'-phenolic hydroxy group is avoided and the all operations of this process are simple. It requires no column chromatography.
2. The overall yield is high. The amount of feed stock will be reduced by 25% so that economic benefits are quite considerable.
3. The monitor and control of the end point for glycosidation is readily facilitated.

The following examples provide a detailed description of this invention. These examples are not intended to limit the invention in any manner.

EXAMPLE 1

Synthesis of 4'-demethylepipodophyllotoxin-4(2,3-di-O-chloroacetyl-4,6-O-ethylidene)-β-D-pyranoglucoside 19. 14 parts of the compound 16 and 14 parts of 4'-demethylepipodophyllotoxin are suspended in 300 parts (volume basis) of dichloromethane. To this suspension is dropwisely added 8 parts of boron trifluoride-etherate solution at temperature below −10° C. (preferably, in the range of −15° to −20° C.). As soon as the solid disappears, to the clear solution are dropwisely added 8 parts (volume basis) of pyridine and the water is then also added thereto. After completing the extraction, the organic phase is washed successively by 5% hydrochloric acid, sodium hydrogen carbonate solution and water followed by drying over anhydrous sodium sulfate. The reaction mixture is evaporated to dryness. The residual solid is recrystallized with methanol. Thus, 16 parts of white solid is obtained, the yield is 60%. (If the mother solution is retreated, the yield would become higher) mp 178–79, $[\alpha]_D = -46.3$ ( C 0.49, chloroform) EI-MS 741 (M).

EXAMPLE 2

Synthesis of 4'-demethylepipodophyllotoxin-4-(4,6-O-ethylidene-β-D-pyranoglucoside (etoposide) 8 parts of the compound 19, 28 parts of zinc acetate and 200 parts of methanol are refluxed at 85° C. for 2 hours. the reaction mixture is evaporated to dryness under the reduced pressure. The residual solid is subjected to extraction while the chloroform/water (2:1) is then added thereto. After completing the extraction, the organic phase is washed with water trice, and followed by drying over anhydrous solution sulfate. By evaporating to dryness, 68 parts of white powdered solid are obtained. Finally, parts of product are given by recrystallizing with methanol. The yield is 90%.

mp 241–243° C.  $[\alpha]_D^{20} = -108$  (Cl, chloroform)

One skilled in the art will readily appreciate that the present invention is well adapted to carry out the objects and obtain the ends and advantages mentioned, as well as those inherent therein. The anti-tumor agent, methods, procedures an techniques described herein are presently representative of the preferred embodiments, are intended to be exemplary and are not intended as limitations on the scope of the present invention changes therein and other uses will occur to those skilled in the art which are encompassed within the spirit of the invention and are defined by the scope of the appended claims.

What is claimed is:
1. A process for preparing the anti-tumor agent etoposide, the process comprising the steps of:
Step 1: condensing 4'-demethyl-epipodophyllotoxin of formula (7):

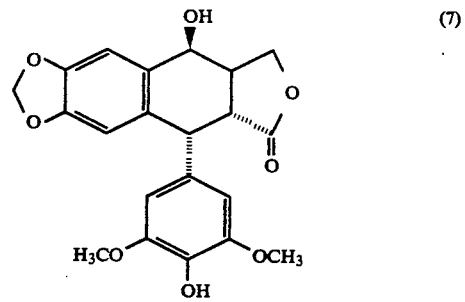

with a compound of formula (16):

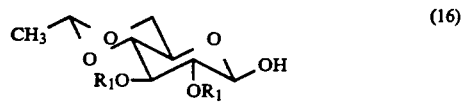

at a temperature of 0° to −30° C., in the presence of a boron trifluoride ether catalyst to give a compound of formula (19):

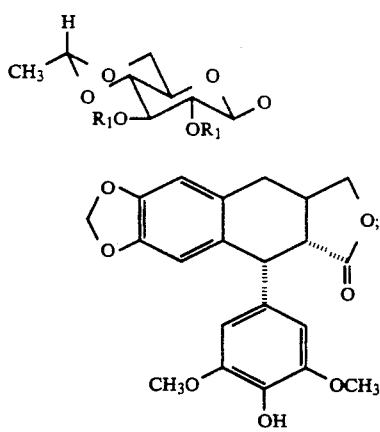
Step 2—reacting the compound of formula (19) obtained in Step 1 with zinc acetate in methanol at a temperature of 80° to 85° C. for 2 hours, to give etoposide of the formula:
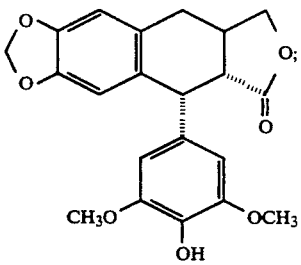
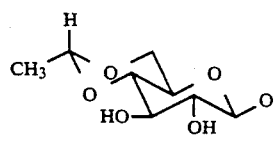
wherein $R_1$ in formulae (16) and (19) is $C(O)CH_2Cl$.
2. The process recited in claim 1, wherein the compounds of formulae (7) and (16) are condensed at a temperature of $-15°$ to $-20°$ C. in Step 1.
* * * * *